US00PP21780P2

(12) United States Plant Patent
Verschoor

(10) Patent No.: US PP21,780 P2
(45) Date of Patent: Mar. 15, 2011

(54) ***VERONICA* PLANT NAMED 'ATOMIC VIOLET'**

(50) Latin Name: *Veronica hybrida*
Varietal Denomination: Atomic Violet

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 12/592,689

(22) Filed: Dec. 1, 2009

(51) Int. Cl.
*A01H 5/00* (2006.01)

(52) U.S. Cl. ..... Plt./251
(58) Field of Classification Search ..... Plt./251
See application file for complete search history.

*Primary Examiner*—Susan B McCormick Ewoldt
(74) *Attorney, Agent, or Firm*—Audrey Charles

(57) ABSTRACT

A new and distinct cultivar of *Veronica* plant named 'Atomic Violet', particularly distinguished by dark purple-violet colored flowers, compact habit, healthy foliage, and good mildew and rust resistance, is disclosed.

2 Drawing Sheets

Latin name of genus and species of plant claimed: *Veronica hybrida.*

Variety denomination: 'Atomic Violet'.

BACKGROUND OF THE INVENTION

The present invention relates to a new and distinct cultivar of *Veronica* plant botanically known as *Veronica hybrida* and hereinafter referred to by the cultivar name 'Atomic Violet'. The new cultivar originated from an open pollination in 2003 in a nursery location in Haarlem, The Netherlands between unknown male and female *Veronica hybrida* plants.

The new cultivar was selected from the results of the open pollination in 2005 in Haarlem, The Netherlands. Asexual reproduction of the new *Veronica* by vegetative cuttings in a controlled environment in Haarlem, The Netherlands since the summer of 2008, has shown that the unique features of the *Veronica* are stable and reproduced true to type in successive generations.

SUMMARY OF THE INVENTION

The following are the most outstanding and distinguishing characteristics of this new cultivar when grown under normal horticultural practices in Haarlem, The Netherlands:

1. Dark purple-violet colored flowers;
2. Compact habit;
3. Healthy foliage; and
4. Good mildew and rust resistance.

Of the many commercially available *Veronica* cultivars, the most similar in comparison to the new cultivar is 'Darwin's Blue', U.S. Plant Pat. No. 13,070. However, in side by side comparisons in Haarlem, The Netherlands, plants of the new cultivar 'Atomic Violet' differ from plants of 'Darwin's Blue' in at least the following characteristics:

1. Plants of the new cultivar have larger flowers, as measured by corolla height and diameter, than plants of 'Darwin's Blue';
2. Plants of the new cultivar have a flower color that is different from plants of 'Darwin's Blue';
3. Plants of the new cultivar have a foliage color that is different from plants of 'Darwin's Blue'; and
4. Plants of the new cultivar have stronger rust and mildew resistance than plants of 'Darwin's Blue'.

Of the many commercially available Echinacea cultivars, another that is similar in comparison to the new cultivar is 'Purpleicious', U.S. Plant Pat. No. 17,639. However, in side by side comparisons in Haarlem, The Netherlands, plants of the new cultivar 'Atomic Violet' differ from plants of 'Purpleicious' in at least the following characteristics:

1. Plants of the new cultivar have larger flowers, as measured by corolla height and diameter, than plants of 'Purpleicious'; and
2. Plants of the new cultivar have a flower color that is slightly different from plants of 'Purpleicious'.

In addition, plants of the new cultivar 'Atomic Violet' are similar to 'Atomic Pink', pending U.S. Plant patent application Ser. No. 12/592,694. However, in side by side comparisons in Haarlem, The Netherlands, plants of the new cultivar 'Atomic Violet' primarily differ from plants of 'Atomic Pink' in floriferousness. Plants of 'Atomic Violet' have more flowers per inflorescence than 'Atomic Pink'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Atomic Violet'. The plant was field grown for approximately 1 year in Haarlem, The Netherlands in an outdoor nursery location. The plant was transplanted into a container for photography purposes.

DETAILED BOTANICAL DESCRIPTION

Figure 1:
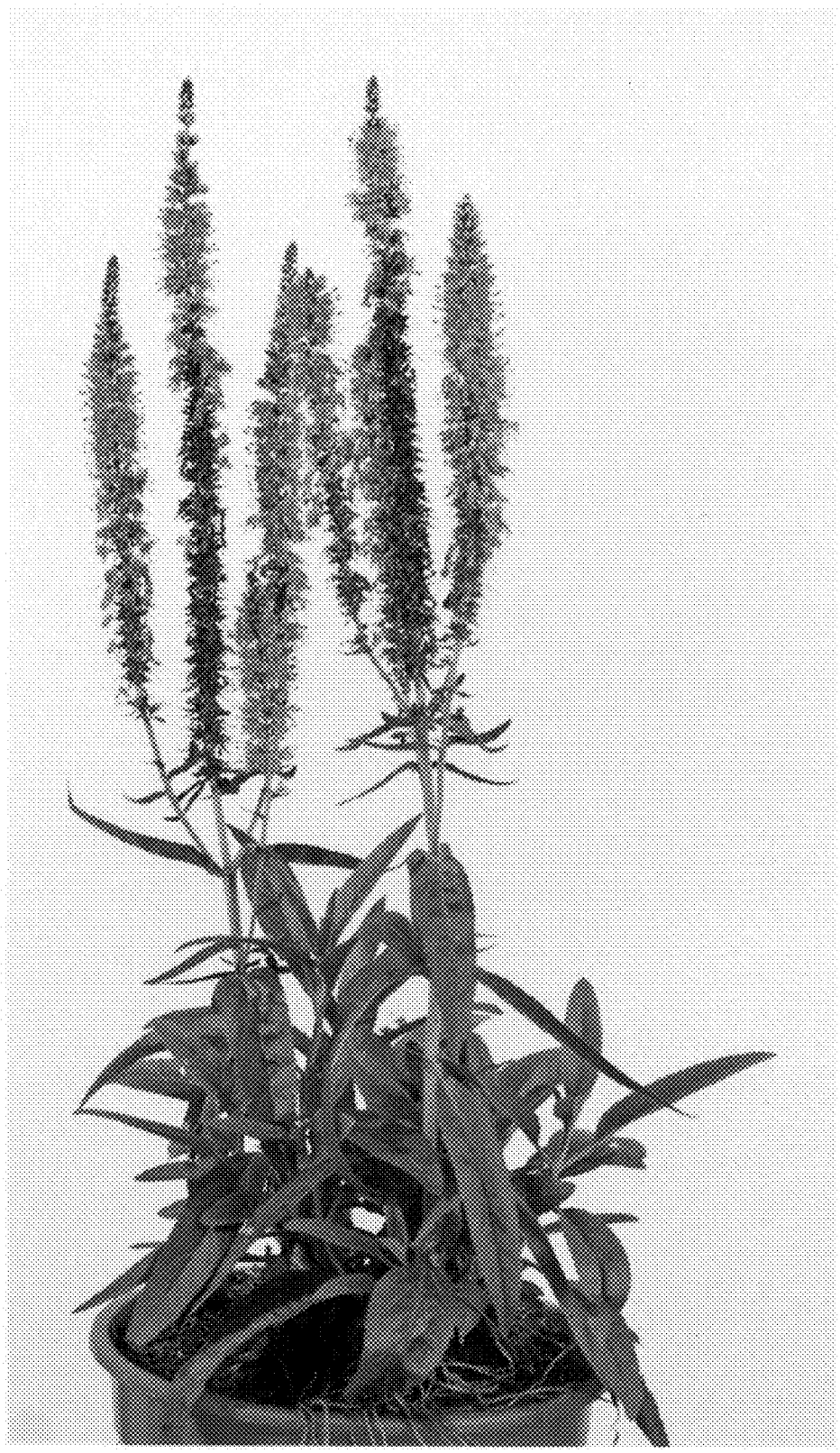
FIG. 1 illustrates a side view of the overall growth and flowering habit of 'Atomic Violet'.
Figure 2:
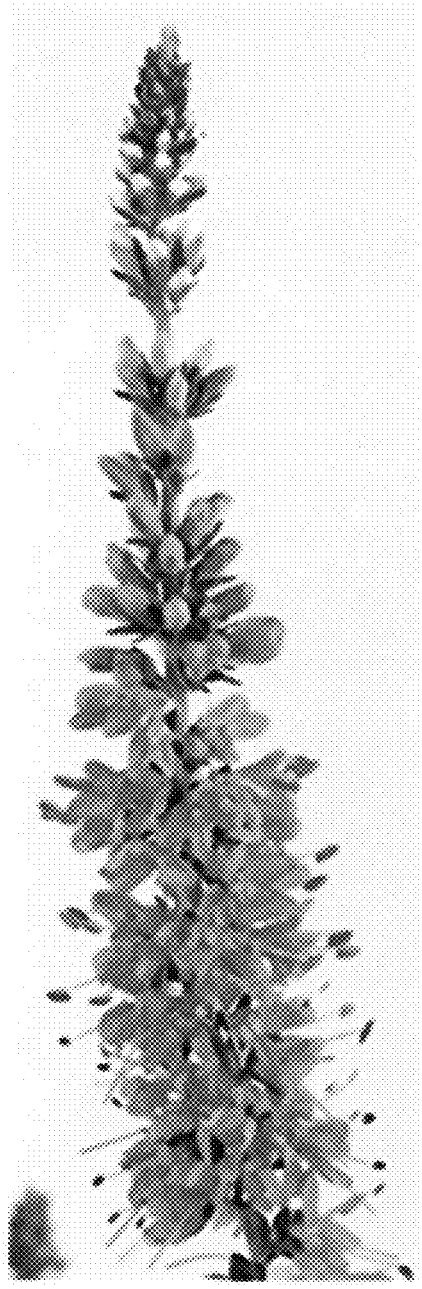
FIG. 2 illustrates a close-up view of an individual inflorescence of 'Atomic Violet'.
Figure 3:
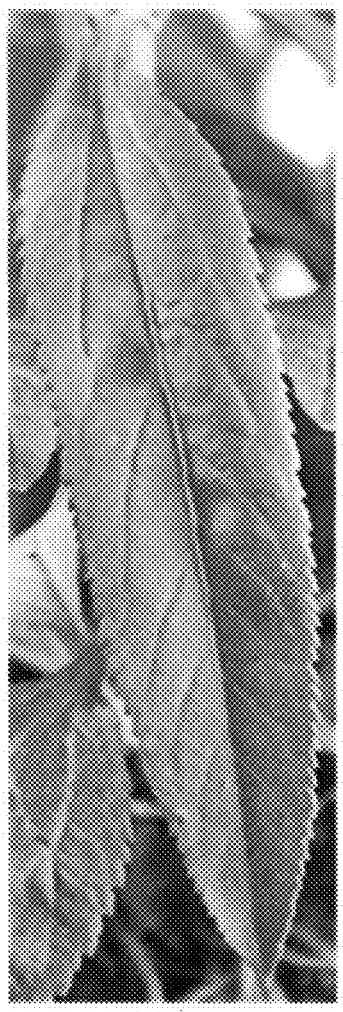
FIG. 3 illustrates a close-up view of the foliage of 'Atomic Violet'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Haarlem, The Netherlands. The plant history was taken in September 2009 on 1-year-old field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Veronica hybrida* cultivar 'Atomic Violet'.

Parentage:

*Female parent.*—Unknown *Veronica hybrida.*

*Male parent.*—Unknown *Veronica hybrida.*

Propagation:

*Type cutting.*—Vegetative cutting.

*Time to produce a rooted cutting.*—Approximately 30 days with average soil temperature of 14° C.

*Root description.*—Fine, fibrous; grey in color.

*Rooting habit.*—Moderate density, poorly branching.

Plant description:

*Type.*—Herbaceous perennial. Overall shape: Narrow inverted triangle. High temperature tolerance: Tolerant to at least 35° C. Low temperature tolerance: Hardy to at least USDA Zone 4. Excellent garden performance.

*Commercial crop time.*—Approximately 4 months from rooted cutting to a finish flowering plant.

*Growth habit and general appearance.*—Upright, moderately vigorous.

*Size.*—Height from soil level to top of plant plane: Approximately 49.5 cm. Width: Approximately 25.5 cm. Rate of growth: In spring, approximately 10 cm per month.

*Branching habit.*—Freely basal branching; pinching not required. Quantity of branches per plant: Approximately 9.

*Branches.*—Shape: Rounded. Strength: Strong. Aspect: Erect. Length to base of inflorescence: Approximately 12.9 cm. Diameter: Approximately 4.0 mm. Length of central internode: Approximately 3.6 cm. Texture: Slightly glossy, densely pubescent with short greenish-white hairs. Length of pubescence: Approximately 0.5 mm. Color of young and mature stems: 143A.

Foliage description:

*General description.*—Quantity of leaves per stem: Approximately 8. Form: Simple. Arrangement: Opposite. Durability to stress: High.

*Leaves.*—Shape: Narrow ovate to lanceolate. Margin: Serrate with approximately 5 teeth per cm. Apex: Acute. Base: Attenuate. Venation pattern: Pinnate. Length of mature leaf: Approximately 9.5 cm. Width of mature leaf: Approximately 2.2 cm. Texture of upper and lower surfaces: Moderately glossy, sparsely pubescent with short greenish-white hairs. Length of pubescence: Approximately 0.3 mm. Color of upper surface of young foliage: 137B and venation of 144B. Color of lower surface of young foliage: 137C with venation of 144B. Color of upper surface of mature foliage: Between 137A and 147A with venation of 144B. Color of lower surface of mature foliage: 147C with venation of 144B.

*Petiole.*—Shape: V-shaped. Length: Approximately 1.1 cm. Width: Approximately 3.5 mm. Height: Approximately 2.0 mm. Color: 138A.

Flowering description:

*Flowering habit.*—Freely flowering under outdoor growing conditions with substantially continuous blooming from July through late September in The Netherlands.

*Lastingness of individual flower on the plant.*—Approximately 7 days.

*Flowering response time.*—Approximately 60 days.

Inflorescence description:

*General description.*—Type: Terminal raceme, persistent. Fragrance: None detected. Height: Approximately 31.2 cm. Width: Approximately 2.4 cm. Quantity of opened flowers per inflorescence: Approximately 550 on central raceme and approximately 300 on secondary racemes. Rate of flower opening: Approximately 10% of the flowers open at any stage.

*Peduncle.*—Strength: Strong. Aspect: Erect to approximately a 30° angle. Length: Approximately 30.7 cm. Diameter: Approximately 2.5 mm. Texture: Smooth, glabrous. Color: 144B.

Flower description:

*General description.*—Type: Single. Shape: Campanulate. Aspect: Outward, turning downward with age.

*Bud just before opening.*—Quantity per inflorescence: Approximately 550 on central raceme and approximately 300 on secondary racemes. Shape: Ovate to oblong. Length: Approximately 7.0 mm. Diameter: Approximately 1.0 cm. Color: Petals of 77B with underside of N77B; calyx of 138B. Rate of opening: Approximately 20% of buds open at once, all open within approximately 7 weeks.

*Corolla.*—Shape: Campanulate. Height: Approximately 1.0 cm. Diameter: Approximately 8.0 mm.

*Petals.*—Quantity: 4. Arrangement: Lower 40% of each petal fused into a narrow tube. Appearance: Dull. Shape: Oblanceolate. Margin: Entire. Apex: Broadly acute. Length: Approximately 6.5 mm. Width: Approximately 3.0 mm. Texture of upper and lower surfaces: Smooth. Color of upper surface when first and fully open: N80B and N80D at base, fades with age to N82A. Color of lower surface when first and fully open: N80B and N80D at base, fades with age to N82A.

*Calyx.*—Shape: Rotate. Length: Approximately 3.0 mm. Diameter: Approximately 4.0 mm.

*Sepals.*—Quantity: 4. Appearance: Dull. Shape: Ovate. Margin: Entire. Apex: Acute. Base: Cuneate, lower 30% fused. Length: Approximately 3.0 mm. Width: Approximately 1.0 mm. Texture of upper and lower surfaces: Smooth. Color of upper and lower surfaces of immature sepals: 138B. Color of upper and lower surfaces of mature sepals: 137B.

*Pedicel.*—Strength: Strong. Aspect: Approximately 50° angle from vertical. Length: Approximately 1.0 mm. Diameter: Approximately 0.5 mm. Texture: Smooth, glabrous. Color: 144B.

*Reproductive organs.*—Androecium: Stamen quantity: 2 per flower, dorsifixed. Anther shape: Elliptic. Anther length: Approximately 2.0 mm. Filament length:

Approximately 7.0 mm. Anther color: 70C. Filament color: N155A. Pollen amount: Sparse to moderate. Pollen color: 4C. Gynoecium: Pistil quantity: 1 per flower. Pistil length: Approximately 8.0 mm. Stigma shape: Clavate. Stigma color: 77B. Style length: Approximately 7.5 mm. Style color: 77B. Ovary color: 144C.

Seed and fruit production: Neither seed nor fruit production has been observed.

Disease and pest resistance: Good mildew and rust resistance. No particular resistance or susceptibility to other diseases or insects noted to date.

What is claimed is:

1. A new and distinct cultivar of *Veronica* plant named 'Atomic Violet', substantially as herein shown and described.

* * * * *